United States Patent
Shen et al.

(10) Patent No.: US 7,510,846 B2
(45) Date of Patent: Mar. 31, 2009

(54) ASSAY EMPLOYING HUMAN OR RAT GAL-R2 GALANIN RECEPTOR

(75) Inventors: Shi-Hsiang Shen, Beaconsfield (CA); Sultan Ahmad, Ile Perrot (CA); Claes Wahlestedt, Stockholm (SE); Philippe Walker, Montreal (CA)

(73) Assignee: National Research Council of Canada, Ottawa, Ontario (CA)

( * ) Notice: Subject to any disclaimer, the term of this patent is extended or adjusted under 35 U.S.C. 154(b) by 0 days.

(21) Appl. No.: 11/407,026

(22) Filed: Apr. 18, 2006

(65) Prior Publication Data

US 2006/0234282 A1 Oct. 19, 2006

Related U.S. Application Data

(60) Division of application No. 10/359,285, filed on Feb. 6, 2003, which is a continuation of application No. 08/981,700, filed as application No. PCT/SE97/01217 on Jul. 4, 1997, now Pat. No. 6,562,945.

(30) Foreign Application Priority Data

Jul. 19, 1996 (SE) .................... 9602822

(51) Int. Cl.
*G01N 33/566* (2006.01)
*C07K 14/705* (2006.01)

(52) U.S. Cl. .................. 435/7.21; 435/7.2; 436/501

(58) Field of Classification Search .......... None
See application file for complete search history.

(56) References Cited

U.S. PATENT DOCUMENTS

| 5,712,111 A | 1/1998 | Linemeyer et al. |
| 5,972,624 A | 10/1999 | Smith et al. |
| 6,410,686 B1 | 6/2002 | Bloomquist et al. |

FOREIGN PATENT DOCUMENTS

| CA | 2256523 | 12/1997 |
| EP | 711830 | 5/1996 |
| WO | WO9215015 | 9/1992 |
| WO | WO9522608 | 8/1995 |
| WO | WO9726853 | 7/1997 |
| WO | WO9829439 | 7/1998 |
| WO | WO9829440 | 7/1998 |
| WO | WO9829441 | 7/1998 |

OTHER PUBLICATIONS

Abstract for French counterpart of WO 95/22608, listed in the Foreign Patent Documents as document 2.
Burgevin et al., "Cloning, pharmacological characterization, and anatomical distribution of a rat cDNA encoding for a galanin receptor," Journal of Molecular Neuroscience (1995) 6:33-41.
Habert-Ortoli et al., "Molecular cloning of a functional human galanin receptor," PNAS (1994) 91(21):9780-9783.
Howard et al., "Molecular cloning and characterization of a new receptor for galanin," FEBS Letters (1997) 405:285-290.

*Primary Examiner*—John D Ulm
(74) *Attorney, Agent, or Firm*—Pepper Hamilton LLP

(57) ABSTRACT

The present invention is directed to a novel receptor for galanin which has been designated as galanin receptor 2. The invention encompasses both the receptor protein as well as nucleic acids encoding the protein. In addition, the present invention is directed to methods and compositions which rely upon either GAL-R2 proteins or nucleic acids.

10 Claims, 11 Drawing Sheets

```
                         25                   50                    75                  100
                          *                    *                     *                    *
CCCCGGCGCACACCGCTCCCTCCACA CCTCCAGGGGAGTGAGCCACTCAA GTCTAAAGCAGAGCCAGTCCCAGGA CTTGAGCGCGGAAGCGAATGGAGT 125                  150                   175                  200
                          *                    *                     *                    *
CAGGGTCATTCGATTGCACCTCTCT CGACTGCGGGCCGGAGCGGGGTACC ATCCTACACTCTGGGTGCTCCCTCC TCCTCCCGTCCCCCGGCCACCCCTC 225                  250                   275                  300
                          *                    *                     *                    *
CCCTGTCTCCTGGAGCTCGGCAGTC TCCCTGGGCGCCTGCAGCGAGGGAG CAGCGTGCTCACCAAGGACCCGGAC AGCTGCGGGAGCGGCGTCCACTTTG 325                  350                   375
                          *                    *                     *
GTGATACC ATG AAT GGC TCC GGC AGC CAG GGC GCG GAG AAC ACG AGC CAG GAA GGC AGT AGC GGC TGG CAG CCT GAG
         M   N   G   S   G   S   Q   G   A   E   N   T   S   Q   E   G   S   S   G   W   Q   P   E 400                  425                   450
                          *                    *                     *
GCG GTC CTT GTA CCC CTA TTT TTC GCG CTC ATC TTC CTC GTG GGC ACC GTG GGC AAC GCG CTG GTG GCG GTG CTG
 A   V   L   V   P   L   F   F   A   L   I   F   L   V   G   T   V   G   N   A   L   V   A   V   L 475                  500                   525
                          *                    *                     *
CTG CGC GGC GGC CAG GCG GTC AGC ACC AAC CTG TTC ATC CTC AAC CTG TTC ATC CTC AAC CTG GGC GTC GCC GAC CTC TGT TTC ATC CTG
 L   R   G   G   Q   A   V   S   T   N   L   F   I   L   N   L   F   I   L   N   L   G   V   A   D   L   C   F   I   L
```

FIG.1A

```
       550                        575                          600
        *                          *                            *
TCC TGC GTG CCT TTC CAG GCC ACC ATC TAC ACC CTG GAC GAC TGG GTG TTC GGC TCC CTG CTC TGC AAG GCT GTT CAT
 C   C   V   P   F   Q   A   T   I   Y   T   L   D   D   W   V   F   G   S   L   L   C   K   A   V   H
       625                        650                          675
        *                          *                            *
TTC CTC ATC TTT CTC ACT ATG CAC GCC AGC AGC TTC ACG GCC CTG GCC GCC GTC TCC CTG GAC AGG TAT CTG GCC ATC CGC
 F   L   I   F   L   T   M   H   A   S   S   F   T   L   A   A   V   S   L   D   R   Y   L   A   I   R
       700                        725                          750
        *                          *                            *
TAC CCG CTG CAC TCC CGA GAG TTG CGC ACA CCT CGA AAC GCC CTG GCC GCC ATC GGG CTC ATC TGG GGG CTA GCA CTG
 Y   P   L   H   S   R   E   L   R   T   P   R   N   A   L   A   A   I   G   L   I   W   G   L   A   L
       775                        800                          825
        *                          *                            *
CTC TTC TCC GGG CCC TAC CTG AGC TAC TAC CGT CAG TCC CAG CTG GCC AAC CTG ACA GTA TGC CAC CCA GCA TGG AGC
 L   F   S   G   P   Y   L   S   Y   Y   R   Q   S   Q   L   A   N   L   T   V   C   H   P   A   W   S
       850                        875                          900                        925
        *                          *                            *                          *
GCA CCT CGA CGT CGA CGT AGA GCC ATG GAC CTC TGC ACC TTC GTC TTT AGC TAC CTG CTA CCA GTC CTC CTC AGT CTG ACC
 A   P   R   R   R   R   A   M   D   L   C   T   F   V   F   S   Y   L   L   P   V   L   L   S   L   T
```

FIG.1B

```
                                                950                         975                        1000
                                                 *                           *                           *
TAT GCG CGT ACC CTG CGC TAC CTC TGG CGC ACA GTC GAC CCG GTG ACT GCA GGC TCA GGT TCC CAG CGC GCC AAA CGC
 Y   A   R   T   L   R   Y   L   W   R   T   V   D   P   V   T   A   G   S   G   S   Q   R   A   K   R 1025                        1050                        1075
                                                 *                           *                           *
AAG GTC ACA CGG ATG ATC ATC GTG GCG GTG CTT TTC TGC CTC TGT TGG ATG CCC CAC CAC GCG CTT ATC CTC TGC
 K   V   T   R   M   I   I   V   A   V   L   F   C   L   C   W   M   P   H   H   A   L   I   L   C 1100                        1125                        1150
                                                 *                           *                           *
GTC TGG TTT GGT CGC TTC CCG CTC ACG CGT GCC ACT TAC GCG CTT CGC ATC CTT TCA CAC CTA GTT TCC TAT GCC AAC
 V   W   F   G   R   F   P   L   T   R   A   T   Y   A   L   R   I   L   S   H   L   V   S   Y   A   N 1175                        1200                        1225
                                                 *                           *                           *
TCC TGT GTC AAC CCC ATC GTT TAC GCT CTG GTC TCC AAG CAT TTC CGT AAA GGT TTC CGC AAA ATC TGC GCG GGC CTG
 S   C   V   N   P   I   V   Y   A   L   V   S   K   H   F   R   K   G   F   R   K   I   C   A   G   L 1250                        1275                        1300
                                                 *                           *                           *
CTG CGC CCT GCC CCG AGG CGA GCT TGG GGC CGA GTG AGC ATC CTG GCG CCT GGG AAC CAT AGT GGC AGC ATG CTG GAA
 L   R   P   A   P   R   R   A   W   G   R   V   S   I   L   A   P   G   N   H   S   G   S   M   L   E
```

FIG.1C

```
                                            1350                                                    1375
      1325                                   *                                                       *
CAG GAA TCC ACA GAC CTG ACA CAG GTG AGC GAG GCA GCC GGG CCC CTT GTC CCA CCC GCA CTT CCC AAC TGC ACA
 Q   E   S   T   D   L   T   Q   V   S   E   A   A   G   P   L   V   P   P   P   A   L   P   N   C   T 1425                                      1450                                       1475
      1400                  *                                         *                                         *
GCC TCG AGT AGA ACC CTG GAT CCG GCT TGT T AAAGGACCAAAGGGCATCTAACAGC TTCTAGACAGTGTGCCGAGGATC
 A   S   S   R   T   L   D   P   A   C 1525                                  1550                                          1575
      1500                               *                                    *                                            *
CCTGGGGGGTTATGCTTGAACGTTAC AGGCTTGAGGCTAAAGACTGAGGAT TGATTGTAGGGAACCTCCAGTTATT AAACGGTGCCGGATTGCTAGAGGGTG 1625                                      1650                                          1675
      1600                              *                                        *                                            *
GCATAGTCCTTCAATCCTGGCACCC GAAAAGCAGATGCAGGAGGACCAGGAGC AGGAGCAAAGCCAGCCATGGAGTTT GAGGCCTGCTTGAACTACCTGAGAT

1700
       *
CCAATAATAAACATTTCATATGCT CTCGTGCCGAATTC
```

FIG.1D

```
                                    30                              60                                90
GGGTCAGGGCACC ATG AAC GTC TCC GGC TGC CCA GGG GCC GGG AAC GCC AGC CAG GCC GGG GGA GGC GGG TGG CAC CCC GAG GCC GTC ATC GTG CCC CTG CTC TTC GCC
              M   N   V   S   G   C   P   G   A   G   N   A   S   Q   A   G   G   G   G   W   H   P   E   A   V   I   V   P   L   L   F   A 120                             150                             180                             210
CTC ATC TTC CTC GTG GGC ACC GTG GGC AAC GGC CTG GTG CTG CGC GCG GTG CTG CGG GGC GGC CAG GCC GTC AGC ACT ACC AAC CTG TTC ATC CTT AAC CTG GGC GTG GCC
 L   I   F   L   V   G   T   V   G   N   G   L   V   L   R   A   V   L   R   G   G   Q   A   V   S   T   T   N   L   F   I   L   N   L   G   V   A 240                             270                             300                             330
GAC CTG TGT TTC ATC CTC TGC TGC GTG CCC TTC CAG GCC ACC ATC TAC ACC CTG GAC GGC TGG GTG TTC GGG TCG CTG CTG TGC AAG GCG GTG CAC TTC CTC ATC TTC CTC
 D   L   C   F   I   L   C   C   V   P   F   Q   A   T   I   Y   T   L   D   G   W   V   F   G   S   L   L   C   K   A   V   H   F   L   I   F   L 360                             390                             420
ACC ATG CAC GCC AGC AGC TTC ACG CTG GCC GCC GTC TCC CTG GAC CGC TAT CTG GCC ATC CGC TAC CCG CTG CAC TCC CGG GAG CTG CGC ACG CCT CGA AAC GCC CTG GCA
 T   M   H   A   S   S   F   T   L   A   A   V   S   L   D   R   Y   L   A   I   R   Y   P   L   H   S   R   E   L   R   T   P   R   N   A   L   A
```

FIG.2A

```
450                 480                 510                 540
 *                   *                   *                   *
GCC ATC GGG CTC ATC TGG GGC CTG TCC CTG CTC TTC TCC GGG CCC TAC CTG AGC TAC TAC CGC CAG TCG CAG CTG GCC AAC CTG ACC GTG TGC CAT CCC GCC TGG AGC GCC
 A   I   G   L   I   W   G   L   S   L   L   F   S   G   P   Y   L   S   Y   Y   R   Q   S   Q   L   A   N   L   T   V   C   H   P   A   W   S   A 570                 600                 630                 660
            *                   *                   *                   *
CCT CCC CGC CGC GCC ATG GAC ATC TGC ACC TTC GTC TTC AGC TAC CTG CTT CCT GTG CTG GTT CTG GGC CTG ACC TAC GCG CGC ACC TTG CGC TAC CTC TGG CGC GCC GTC
 P   R   R   R   A   M   D   I   C   T   F   V   F   S   Y   L   L   P   V   L   V   L   G   L   T   Y   A   R   T   L   R   Y   L   W   R   A   V 690                 720                 750
            *                   *                   *
GAC CCG GTG GCC GCC GGC TCG GGT GCC CGG CGC GCC AAG CGC AAG GTC ACA CGG ATG ATC CTC ATC GTG GCG GCG CTC TTC TGC CTC TGC TGG ATG CCC CAC CAC GCG CTC
 D   P   V   A   A   G   S   G   A   R   R   R   A   K   R   K   V   T   R   M   I   L   I   V   A   A   L   F   C   L   C   W   M   P   H   H   A   L
```

FIG.2B

```
      780                   810                     840                        870
       *                     *                       *                          *
ATC CTC TGC GTG TGG TTC GGC CAG TTC CCG CTC ACG CGG GCC ACT TAT GCG CTT CGG ATC CTC TCG CAC CTG GTC TCC TAC GCC AAC TCC TGC GTC AAC CCC ATC GTT TAC
 I   L   C   V   W   F   G   Q   F   P   L   T   R   A   T   Y   A   L   R   I   L   S   H   L   V   S   Y   A   N   S   C   V   N   P   I   V   Y 900                    930                      960                         990
                    *                      *                        *                           *
GCG CTG GTC TCC AAG CAC TTC CGA AAA GGC TTC ACG AGG ATC TGC GCG GGC CTG CTG GGC CGT GCC CCA GGC CGA GCC TCC GGC CGT GTG TGC GCT GCG GCC CGG GGC ACC
 A   L   V   S   K   H   F   R   K   G   F   T   R   I   C   A   G   L   L   G   R   A   P   G   R   A   S   G   R   V   C   A   A   A   R   G   T 1020                     1050                     1080                      1110
                 *                        *                        *                          *
CAC AGT GGC TCC GTG TTG GAG CGG GAG TCC AGC GAC CTG TTG CAC ATG AGC GAG GCG GGG GCC CTT CCT CGG CCT TGC CCC GGC GCT TCC CAG CCA TGC ATC CTC GAG CCC
 H   S   G   S   V   L   E   R   E   S   S   D   L   L   H   M   S   E   A   A   G   A   L   R   P   C   P   G   A   S   Q   P   C   I   L   E   P 1140                    1170                     1200
              *                       *                        *
TGT CCT GGC CCC TCC TGG CAG GGC CCA AAG GCA GGG CAG ACA GGC ATT CCT GAC GGT TGA TGTGGCCT TGAAAGGCACTTACCGGGCG CCTGGGATGTACACAGTG
 C   P   G   P   S   W   Q   G   P   K   A   G   Q   T   G   I   P   D   G   *

# ASSAY EMPLOYING HUMAN OR RAT GAL-R2 GALANIN RECEPTOR

CROSS-REFERENCE TO RELATED APPLICATIONS

This application is a divisional of U.S. Ser. No. 10/359,285 filed Feb. 6, 2003, which is a continuation of U.S. Ser. No. 08/981,700 filed Jan. 7, 1998, which issued as U.S. Pat. No. 6,562,945 on May 13, 2003, which is the U.S. National Stage filing of International Application Serial No. PCT/SE97/01217 filed Jul. 4, 1997, which claims priority to Swedish Application SE 9602822-0 filed Jul. 19, 1996.

FIELD OF THE INVENTION

The present invention is in the general field of biological receptors and the various uses that can be made of such receptors. More specifically, the invention relates to nucleic acids encoding a novel galanin receptor and the receptor protein itself.

BACKGROUND AND PRIOR ART

Galanin is a small (29-30 amino acid) neuroendocrine peptide which does not belong to any known peptide family (Bedecs et al., *Int. J. Biochem. Cell. Biol.* 27: 337-349 (1995)). It is widely distributed in the central nervous system and other tissues, and has been reported to have a large number of diverse biological and pharmacological activities. Galanin has been reported to: (a) promote growth hormone release (Bauer et al., *The Lancet* 2:192-195 (1986)); (b) inhibit glucose-induced insulin release (Ahren et al., *FEBS Lett.* 299:233-237 (1988)); (c) regulate motility in the gastrointestinal tract (Fox-Thelkeld et al., *Gastroenter-ology* 101: 1471-1476 (1991)); (d) stimulate feeding behavior (Crawley et al., *J. Neurosci* 10:3695-3700 (1990)); and (e) impair cognitive function (Mastropaolo et al., *Proc. Nat'l Acad. Sci. U.S.A.* 85:9841-9845 (1988)).

Of particular pharmacological interest are galanin's analgesic effects (Post et al., *Acta Physiol. Scand.* 132:583-584 (1988)). In the spinal cord, galanin inhibits nociceptive reflexes and potentiates the analgesic effect of morphine (Wiesenfeld-Hallin et al., *Neurosci. Lett.* 105:149-154 (1989)). Target administration of galanin hyperpolarizes dorsal horn neurons and chronic administration of a galanin receptor antagonist after axotomy has been reported to markedly increase autonomy in rats (Verge et al., *Neurosci. Lett.* 149:193-197 (1993)). These observations indicate that galanin, like morphine, has strong anti-nociceptive actions in vivo. Thus, the known pharmacological effects of galanin suggest potential therapeutic applications as an anesthetic or analgesic in animals and humans.

Galanin exerts its effects by binding to membrane-bound receptors. The cDNA for one such receptor ("GAL-R1") has been cloned from both humans and rats (Habert-Ortoliet et al., *Proc. Natl. Acad. Sci. U.S.A.* 91:9780-9783 (1994); Burgevin et al., *J. Mol. Neurosci.* 6:33-41 (1995)). High levels of rat GAL-R1 mRNA have been found in the ventral hippocampus, thalamus, amygdala, and medulla oblongata of the brain and in the dorsal horn of the spinal cord (Burgevin et al., supra). Pharmacological data obtained using galanin fragments, agonists and antagonists have suggested that more than one type of receptor may be responsible for galanin's actions (for a review, see Valkna et al., *Neurosci. Lett.* 187: 75-78 (1995)). The isolation and characterization of new receptors for galanin would be highly desirable to assist in the discovery and development of therapeutic agents for altering galanin activity in vivo.

SUMMARY OF THE INVENTION

The present invention is based upon the discovery of a novel galanin receptor ("GAL-R2") which is distinct from previously reported receptors in terms of structure, tissue distribution and binding characteristics. Receptors from both the rat and human have been isolated and sequenced. As used herein, the term "GAL-R2" refers to the receptor from either of these species unless the text, expressly or by context, indicates otherwise.

In its first aspect, the invention is directed to proteins, except as existing in nature, comprising the amino acid sequence consisting functionally of rat GAL-R2 (as shown in FIG. 1) or consisting functionally of human GAL-R2 (as shown in FIG. 2). The term "consisting functionally of" refers to proteins in which the sequence of FIG. 1 or FIG. 2 has undergone additions, deletions or substitutions which do not substantially alter the functional characteristics of the receptor. Thus, the invention encompasses proteins having exactly the same amino acid sequence as shown in the figures, as well as proteins with differences that are not substantial as evidenced by their retaining the basic, qualitative ligand binding properties of GAL-R2. The invention further encompasses substantially pure proteins consisting essentially of a GAL-R2 amino acid sequence, antibodies that bind specifically to GAL-R2 (i.e. that have at least a 100 fold greater affinity for GAL-R2 than any other protein), and antibodies made by a process involving the injection of pharmaceutically acceptable preparations of such proteins into an animal capable of antibody production. In a preferred embodiment, monoclonal antibody to GAL-R2 is produced by injecting the pharmaceutically acceptable preparation of GAL-R2 into a mouse and then fusing mouse spleen cells with myeloma cells.

The invention is also directed to a substantially pure polynucleotide encoding a protein comprising the amino acid sequence consisting functionally of the sequence of rat GAL-R2 (as shown in FIG. 1; SEQ ID NO:2) or human GAL-R2 (as shown in FIG. 2; SEQ ID NO:4). This aspect of the invention encompasses polynucleotides encoding proteins consisting essentially of the amino acid sequences of in the figures, expression vectors comprising such polynucleotides, and host cells transformed with such vectors. Also included is the recombinant rat and human GAL-R2 proteins produced by host cells made in this manner. Preferably, the polynucleotide encoding rat GAL-R2 has the nucleotide sequence shown in FIG. 1 (SEQ ID NO:1) and the polynucleotide encoding human GAL-R2 has the nucleotide sequence shown in FIG. 2 (SEQ ID NO:3)It is also preferred that the vectors and host cells used for the expression of GAL-R2 use these particular polynucleotides.

In another aspect, the present invention is directed to a method for assaying a test compound for its ability to bind to GAL-R2. This method is performed by incubating a source of GAL-R2 with a ligand known to bind to the receptor and with the test compound. The source of GAL-R2 should be substantially free of other types of galanin receptors, i.e. greater than 90% of the galanin receptors present should correspond to GAL-R2. Upon completion of incubation, the ability of the test compound to bind to GAL-R2 is determined by the extent to which ligand binding has been displaced. A preferred source of GAL-R2 for use in the assay is a cell transformed with a vector for expressing the receptor and comprising a polynucleotide encoding a protein consisting essentially of the amino acid sequence shown in FIG. 1 (rat GAL-R2; SEQ ID NO:2) and FIG. 2 (human GAL-R2; SEQ ID NO:4). Instead of using cells in the assay, a membrane preparation can be prepared from the cells and this can be used as the source of GAL-R2. Although not essential, the assay can be accompanied by the determination of the activation of a second messenger pathway such as the adenyl cyclase pathway. This should help to determine whether a compound that binds to GAL-R2 is acting as an agonist or antagonist to galanin.

In another aspect, the present invention is directed to a method for assaying a test compound for its ability to alter the expression of GAL-R2. This method is performed by growing cells expressing GAL-R2, but substantially free of other galanin receptors, in the presence of the test compound. Cells are then collected and the expression of GAL-R2 is compared with expression in control cells grown under essentially identical conditions but in the absence of the test compound. In preferred embodiments, the cells expressing GAL-R2 are cells transformed with an expression vector comprising a polynucleotide sequence encoding a protein consisting essentially of the amino acid sequence shown in FIG. 1 (rat GAL-R2; SEQ ID NO:2) or FIG. 2 (human GAL-R2: SEQ ID NO:4). A preferred test compound is an oligonucleotide at least 15 nucleotides in length and comprising a sequence complimentary to a sequence shown in one or both of the figures. The preferred method for determining receptor expression is by means of a receptor binding assay.

BRIEF DESCRIPTION OF THE DRAWINGS

FIG. 1: The composite nucleotide sequence and corresponding translated amino acid sequence (in single letter code) of rat GAL-R2 is shown. The nucleic acid sequence has been given the designation SEQ ID NO:1 and the amino acid sequence, SEQ ID NO:2.

FIG. 2: The composite nucleotide sequence and corresponding translated amino acid sequence (in single letter code) of human GAL-R2 is shown. The nucleic acid sequence has been given the designation SEQ ID NO:3 and the amino acid sequence, SEQ ID NO:4.

FIG. 3: The amino acid sequences of rat GAL-R2 (RGALR2.PRO), (SEQ ID NO:2),rat GAL-R1 (rGALR1.PRO), human GAL-R2 (HGALR2.PRO) (SEQ ID NO:4) and human GAL-R1 (hGALR1.PRO) are aligned to show regions of homology. The residues in the HGAL-R2 sequence that are shared 20 with other sequences are boxed. In order to optimize alignment, gaps were created at several places in GAL-R2 sequences and these gaps are indicated by black boxes. The rGALR1.PRO sequence has been designated as SEQ ID NO:5; and the hGALR1.PRO sequence as SEQ ID NO:6.

FIG. 4 shows the results of binding assays in which unlabeled galanin and galanin-related peptides were allowed to compete with labeled galanin for GAL-R2 sites. The data has been converted to percentages, with binding in the absence of competitor serving as 100%. No inhibition was observed when binding assays were performed in the presence of peptides unrelated to galanin.

Definitions

Figure 4:
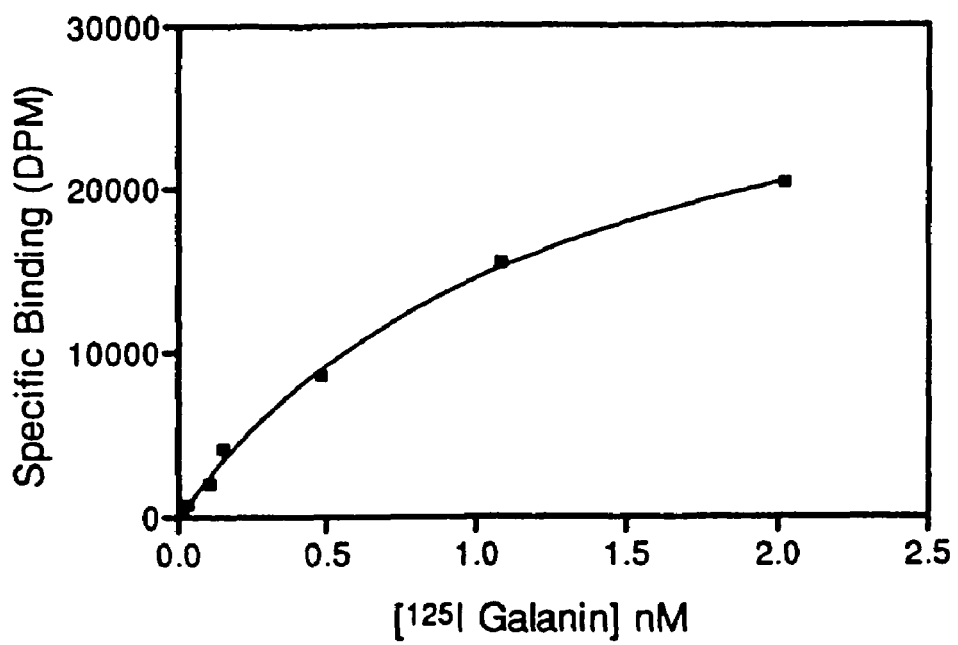
FIG. 4: The saturation isotherm of $^{125}$I-galanin binding to membranes from rat GAL-R2-expressing HEK-293 cells is shown. Increasing concentrations of radiotracer were incubated with the membranes, binding was allowed to reach equilibrium, and then the reaction was filtered as described under Example 3. Nonspecific binding was measured in the presence of 1 µM of unlabeled galanin and was subtracted from total binding to obtain specific binding.

The description that follows uses a number of terms that refer to recombinant DNA technology. In order to provide a clear and consistent understanding of the specification and claims, including the scope to be given such terms, the following definitions are provided.

Cloning vector: A plasmid or phage DNA or other DNA sequence which is able to replicate autonomously in a host cell, and which is characterized by one or a small number of restriction endonuclease recognition sites. A foreign DNA fragment may be spliced into the vector at these sites in order to bring about the replication and cloning of the fragment. The vector may contain a marker suitable for use in the identification of transformed cells. For example, markers may provide tetracycline resistance or ampicillin resistance.

Expression vector: A vector similar to a cloning vector but which is capable of inducing the expression of the DNA that has been cloned into it, after transformation into a host. The cloned DNA is usually placed under the control of (i.e., operably linked to) certain regulatory sequences such as promoters or enhancers. Promoter sequences may be constitutive, inducible or repressible.

Substantially pure: As used herein, "substantially pure" means that the desired product is essentially free from contaminating cellular components. Contaminants may include, but are not limited to, proteins, carbohydrates or lipids. One method for determining the purity of a protein or nucleic acid is by electrophoresing a preparation in a matrix such as polyacrylamide or agarose. Purity is evidenced by the appearance of a single band after staining.

Host: Any prokaryotic or eukaryotic cell that is the recipient of a replicable expression vector or cloning vector is the "host" for that vector. The term encompasses prokaryotic or eukaryotic cells that have been engineered to incorporate a desired gene on its chromosome or in its genome. Examples of cells that can serve as hosts are well known in the art, as are techniques for cellular transformation (see e.g. Sambrook et al., Molecular Cloning: A Laboratory Manual, 2nd ed. Cold Spring Harbor (1989)).

Promoter: A DNA sequence typically found in the 5' region of a gene, located proximal to the start codon. Transcription is initiated at the promoter. If the promoter is of the inducible type, then the rate of transcription increases in response to an inducing agent.

Complementary Nucleotide Sequence: A complementary nucleotide sequence, as used herein, refers to the sequence that would arise by normal base pairing. For example, the nucleotide sequence 5'-AGAC-3' would have the complementary sequence 5'-GTCT-3'.

Expression: Expression is the process by which a polypeptide is produced from DNA. The process involves the transcription of the gene into mRNA and the translation of this mRNA into a polypeptide.

DETAILED DESCRIPTION OF THE INVENTION

The present invention is directed to the GAL-R2 receptor proteins, genetic sequences coding for the receptors, a method for assaying compounds for binding to GAL-R2 and a method for assaying compounds for their ability to alter GAL-R2 expression. The receptors and their nucleic acids are defined by their structures (as shown in FIGS. 1 and 2) as well as by their tissue distribution and binding characteristics.

With respect to structure, it will be understood that the present invention encompasses not only sequences identical to those shown in the figures, but also sequences that are essentially the same and sequences that are otherwise substantially the same and which result in a receptor retaining the basic binding characteristics of GAL-R2. For example, it is well known that techniques such as site-directed mutagenesis may be used to introduce variations in a protein's structure. Variations in GAL-R2 introduced by this or some similar method are encompassed by the invention provided that the resulting receptor retains the ability to specifically bind to galanin or galanin-like peptides. Thus, the invention relates to proteins comprising amino acid sequences consisting functionally of the sequence of SEQ ID NO:2 (rat) and SEQ ID NO:4 (human).

I. Nucleic Acid Sequences Coding for GAL-R2

DNA sequences coding for GAL-R2 are present in a variety of tissues, any of which may serve as a source for the isolation of nucleic acid coding for the receptor. In rats, spinal cord and brain tissues are among the preferred sources with the dorsal ganglia of the spinal cord and the hippocampus, mammillary bodies and cerebellum of the brain being especially preferred. In addition, cells and cell lines that express GAL-R2 may serve as a source for nucleic acid. These may either be cultured cells that have not undergone transformation or cell lines specifically engineered to express recombinant GAL-R2.

Many methods are available for isolating DNA sequences and may be adapted for the isolation of GAL-R2 nucleic acid (see for example Sambrook et al., Molecular Cloning: A Laboratory Manual, 2nd ed., Cold Spring Harbor Press (1989)). One preferred method for rat GAL-R2, illustrated in Example 1, is to screen a cDNA library that has been prepared by reverse transcribing mRNA isolated from tissues or cells known to express GAL-R2. The library may be prepared from, for example, rat dorsal root ganglia or from brain tissue. A rat brain stem spinal cord cDNA library in ZAP II has been found to produce suitable results. A similar method can be used for human GAL-R2 or, alternatively, a human DNA library can be screened as described in Example 7.

It is expected that a wide variety of probes specific for GAL-R2 can be used equally well for the screening of cDNA libraries. One way to easily produce a large amount of probe is to use the polymerase chain reaction (PCR) to amplify the desired sequence from a cDNA library. For example, PCR may be performed on a cDNA library from rat dorsal root ganglia using the primers:

```
                                        (SEQ ID NO:7)
TM2: 5'-GGCCGTCGACTTCATCGTC(A or T)(A or C)(T or
C)CTI(G or T)CI(T or C)TIGC(A,C,G or T)GAC-3'

(SEQ ID NO:8)
TM7: 5'-(A or G)(C,A or T)(A or T)(A or G)CA(A or
G)TAIATIATIGG(A or G)TT-3'
```

The letter "I" in the sequences above, is the abbreviation for inosine.

Amplified fragments can be size fractionated on an agarose gel and the selected fragments (e.g., fragments 400-1,000 base pairs in length) inserted into an appropriate vector (e.g., pGEM-T). The vector may be introduced into competent cells (e.g., DH5 cells) by any of the established methods for cell transformation, e.g., by calcium phosphate precipitation. Transformed cells containing the DNA of interest may be identified by again performing PCR with the TM2 and TM7 primers. The DNA inserts present in these cells are excised, purified and labeled with $^{32}P$. The labeled DNA fragments thus produced are used as probes for screening a cDNA library for GAL-R2. The presence of the correct sequence in selected cells may be confirmed by DNA sequencing and, if necessary, partial clones may be spliced together to form a full-length sequence.

Although the above procedure is known to be suitable for obtaining GAL-R2 nucleic acid, it is expected that alternative techniques can be developed with relatively little effort. Thus, cDNA libraries may be screened using probes synthesized based upon the GAL-R2 sequence shown in FIG. 1 for rats and shown in FIG. 2 for humans. In general, probes should be at least 14 nucleotides long and should not be selected from regions known to be highly conserved among proteins, e.g., the transmembrane domains of G-protein linked receptors. Alternatively, using the sequences shown in the figures, it should be possible to select PCR primers that amplify the full-length GAL-R2 sequence. The same techniques that have proven successful in the rat and human can be used to obtain GAL-R2 sequences from other species as well.

II. Production and Isolation of GAL-R2 Recombinant Protein

In order to express recombinant GAL-R2, the structural sequence for the protein described above must be placed in a vector containing transcriptional and translational signals recognizable by an appropriate host. The cloned GAL-R2 sequences, preferably in double-stranded form, are inserted into the expression vector in an operable linkage, i.e., they are positioned so as to be under the control of the vector's regulatory sequences and in such a manner that mRNA is produced which is translated into the GAL-R2 amino acid sequence.

Expression of the GAL-R2 receptor protein in different hosts may result in different post-translational modifications that can, potentially, alter the properties of the receptor. Preferably, nucleic acid encoding GAL-R2 is expressed in eukaryotic cells, especially mammalian cells. These cells provide post-translational modifications which, inter alia, aid in the correct folding of the receptor protein. Examples of an appropriate vector, pCDNA3-GAL-R2, and host, HEK293 cells, are given in the Example 2.

Other mammalian cells that may be used include, without limitation, NIH-3T3 cells, CHO cells, HeLa cells, LM(tk−) cells etc. Vectors suitable for use in each of these various cell types are well known in the art (see e.g. Sambrook et al., supra). Preferred eukaryotic promoters include that of the mouse metallothionein I gene; the TK promoter of Herpes virus; the SV40 early promoter; and the yeast GAL4 gene promoter. Some examples of suitable prokaryotic promoters include those capable of recognizing T4 polymerases, the $P_R$ and $P_L$ promoters of bacteriophage lambda, and the trp, recA, heat shock and lacZ promoters of E. coli.

Expression vectors may be introduced into host cells by methods such as calcium phosphate precipitation, microinjection or electroporation. Cells expressing the GAL-R2 receptor can be selected using methods well known in the art.

One simple method for confirming the presence of the receptor nucleic acid in cells is to perform PCR amplification using the procedures and primers discussed above. The presence of functional receptor may be confirmed by performing binding assays using labeled galanin.

Once cells producing recombinant GAL-R2 receptor have been identified, they may be used in either binding assays or in assays designed to identify agents capable of altering GAL-R2 expression. Alternatively, membranes may be isolated from the cells and used in receptor binding assays.

III. Antibodies to GAL-R2

The present invention also is directed to antibodies that bind specifically to GAL-R2 and to a process for producing such antibodies. Antibodies that "bind specifically to GAL-R2" are defined as those that have at least a one hundred fold greater affinity for GAL-R2 than for GAL-R1 and any undenatured protein not binding galanin. The process for producing such antibodies may involve either injecting the GAL-R2 protein itself into an appropriate animal or, preferably, injecting short peptides made to correspond to different regions of GAL-R2. The peptides should be at least five amino acids in length and should be selected from regions believed to be unique to the GAL-R2 protein. Thus, highly conserved transmembrane regions should generally be avoided in selecting peptides for the generation of antibodies. Methods for making and detecting antibodies are well known to those of skill in the art as evidenced by standard reference works such as: Harlow et al., Antibodies, A Laboratory Manual, Cold Spring Harbor Laboratory, N.Y. (1988)); Klein, Immunology: The Science of Self-Nonself Discrimination (1982); Kennett, et al., Monoclonal Antibodies and Hybridomas: A New Dimension in Biological Analyses (1980); and Campbell, "Monoclonal Antibody Technology," in Laboratory Techniques in Biochemistry and Molecular Biology, (1984)).

"Antibody," as used herein, is meant to include intact molecules as well as fragments which retain their ability to bind to antigen (e.g., Fab and F(ab)$_2$ fragments). These fragments are typically produced by proteolytically cleaving intact antibodies using enzymes such as papain (to produce Fab fragments) or pepsin (to produce F(ab)$_2$ fragments). The term "antibody" also refers to both monoclonal antibodies and polyclonal antibodies. Polyclonal antibodies are derived from the sera of animals immunized with the antigen. Monoclonal antibodies can be prepared using hybridoma technology (Kohler, et al., *Nature* 256:495 (1975); Hammerling, et al., in: Monoclonal Antibodies and T-Cell Hybridomas, Elsevier, M. Y., pp. 563-681 (1981)). In general, this technology involves immunizing an animal, usually a mouse, with either intact GAL-R2 or a fragment derived from GAL-R2. The splenocytes of the immunized animals are extracted and fused with suitable myeloma cells, e.g., SP$_2$O cells. After fusion, the resulting hybridoma cells are selectively maintained in HAT medium and then cloned by limiting dilution (Wands, et al., *Gastroenterology* 80:225-232 (1981)). The cells obtained through such selection are then assayed to identify clones which secrete antibodies capable of binding to GAL-R2.

The antibodies, or fragments of antibodies, of the present invention may be used to detect the presence of GAL-R2 protein using any of a variety of immunoassays. For example, the antibodies may be used in radioimmunoassays or in immunometric assays, also known as "two-site" or "sandwich" assays (see Chard, T., "An Introduction to Radioimmune Assay and Related Techniques," in Laboratory Techniques in Biochemistry and Molecular Biology, North Holland Publishing Co., N.Y. (1978)). In a typical immunometric assay, a quantity of unlabelled antibody is bound to a solid support that is insoluble in the fluid being tested, e.g., blood, lymph, cellular extracts, etc. After the initial binding of antigen to immobilized antibody, a quantity of detectably labeled second antibody (which may or may not be the same as the first) is added to permit detection and/or quantitation of bound antigen (see e.g. Radioimmune Assay Method, Kirkham et al., e.d., pp. 199-206, E & S. Livingstone, Edinburgh (1970)). Many variations of these types of assays are known in the art and may be employed for the detection of GAL-R2.

Antibodies to GAL-R2 may also be used in the purification of either the intact receptor or fragments of the receptor (see generally, Dean et al., Affinity Chromatography, A Practical Approach, IRL Press (1986)). Typically, antibody is immobilized on a chromatographic matrix such as Sepharose 4B. The matrix is then packed into a column and the preparation containing GAL-R2 is passed through under conditions that promote binding, e.g., under conditions of low salt. The column is then washed and bound GAL-R2 is eluted using a buffer that promotes dissociation from antibody, e.g., buffer having an altered pH or salt concentration. The eluted GAL-R2 may be transferred into a buffer of choice, e.g., by dialysis, and either stored or used directly.

IV. Assay for GAL-R2 Binding

One of the main uses for GAL-R2 nucleic acids and recombinant proteins is in assays designed to identify agents, other than galanin, capable of binding to GAL-R2 receptors. Such agents may either be agonists, mimicking the effects of galanin, or antagonists, inhibiting the effects of galanin. Of particular interest is the identification of agents which bind to the GAL-R2 receptors and modulate adenyl cyclase activity in the cells. These agents have potential therapeutic application as either analgesics or anesthetics.

An example of an assay that may be used for detecting compounds binding to GAL-R2 is presented in Example 4. The essential feature of this assay is that a source of GAL-R2 is incubated together with a ligand known to bind to the receptor and with the compound being tested for binding activity. The preferred source for GAL-R2 is cells, preferably mammalian cells, transformed to recombinantly express the receptor. The cells selected should not express a substantial amount of any other receptor which binds galanin, e.g., GAL-R1. This can easily be determined by performing galanin binding assays on cells derived from the same tissue or cell line as those recombinantly expressing GAL-R2 but which have not undergone transformation.

The assay may be performed either with intact cells or, preferably, with membranes prepared from the cells (see e.g. Wang, et al., *Proc. Natl. Acad. Sci. U.S.A.* 90:10230-10234 (1993)). The membranes are incubated with a ligand specific for galanin receptors and with a preparation of the compound being tested. After binding is complete, receptor is separated from the solution containing ligand and test compound, e.g. by filtration, and the amount of binding that has occurred is determined. Preferably, the ligand used is galanin detectably labeled with a radioisotope such as $^{125}$I. However, if desired, fluorescent or chemiluminescent labels can be used instead. Among the most commonly used fluorescent labeling compounds are fluorescein isothiocynate, rhodamine, phycoerythrin, phycocyanin, allophycocyanin, o-phthaldehyde and fluorescamine. Useful chemiluminescent compounds include luminol, isoluminol, theromatic acridinium ester, imidazole, acridinium salt, and oxalate ester. Any of these agents which can be used to detectably label galanin will produce a ligand suitable for use in the assay.

Nonspecific binding may be determined by carrying out the binding reaction in the presence of a large excess of unlabelled ligand. For example, $^{125}$I-galanin may be incubated with receptor and test compound in the presence of a thousandfold excess of unlabelled galanin. Nonspecific binding should be subtracted from total binding, i.e. binding in the absence of unlabeled galanin, to arrive at the specific binding for each sample tested. Other steps such as washing, stirring, shaking, filtering and the like may be included in the assays as necessary. Typically, wash steps are included after the separation of membrane-bound ligand from ligand remaining in solution and prior to quantitation of the amount of ligand bound, e.g., by counting radioactive isotope. The specific binding obtained in the presence of test compound is compared with that obtained in the presence of labeled ligand alone to determine the extent to which the test compound has displaced galanin.

Figure 5:
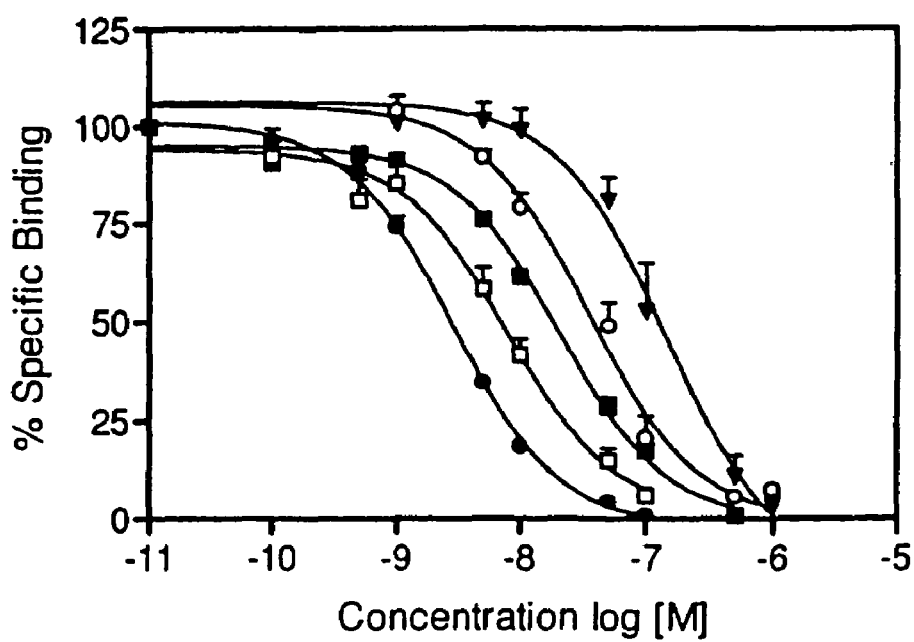
FIG. 5.

In performing binding assays, care must be taken to avoid artifacts which may make it appear that a test compound is interacting with the GAL-R2 receptor when, in fact, binding is being inhibited by some other mechanism. For example, the compound being tested should be in a buffer which does not itself substantially inhibit the binding of galanin to GAL-R2 and should, preferably, be tested at several different concentrations. Preparations of test compound should also be examined for proteolytic activity and it is desirable that antiproteases be included in assays. Finally, it is highly desirable that compounds identified as displacing the binding of ligand to GAL-R2 receptor be reexamined in a concentration range sufficient to perform a Scatchard analysis on the results. This type of analysis is well known in the art and can be used for determining the affinity of a test compounds for receptor (see e.g., Ausubel, et al., Current Protocols in Molecular Biology, 11.2.1-11.2.19 (1993); Laboratory Techniques and Biochemistry and Molecular Biology, Work, et al., ed., N.Y. (1978) etc.). Computer programs may be used to help in the analysis of results (see e.g., Munson, P., *Methods Enzymol.* 92:543-577 (1983); McPherson, G. A., Kinetic, EBDA Ligand, Lowry-A Collection of Radioligand Binding Analysis Programs, Elsevier-Biosoft, U.K. (1985)). An example of the types of curves that may be obtained using this method is shown in FIG. 5 and examples of inhibitory constants for galanin-related peptides determined using binding assays are shown in Table 1.

The activation of a second messenger pathway may be examined by performing adenyl cyclase assays for compounds that have been identified as binding to the GAL-R2 receptor. These assays may be carried out as discussed in Example 5 or using any other method for determining cAMP concentration. Typically, adenyl cyclase assays will be performed separately from binding assays, but it may also be possible to perform binding and adenyl cyclase assays on a single preparation of cells.

V. Assay for Ability to Modulate GAL-R2 Expression

One way to either increase or decrease the biological effects of galanin is to alter the extent to which GAL-R2 is expressed in cells. Therefore, assays for the identification of compounds that either inhibit or enhance expression are of considerable interest. These assays are carried out by growing cells expressing GAL-R2 in the presence of a test compound and then comparing receptor expression in these cells with cells grown under essentially identical conditions but in the absence of the test compound. As in the binding assays discussed above, it is desirable that the cells used be substantially free of receptors for galanin other than GAL-R2. Scatchard analysis of binding assays performed with labeled galanin can be used to determine receptor number. The binding assays may be carried out as discussed above in section IV and will preferably utilize cells that have been engineered to recombinantly express GAL-R2 as described in sections I and II.

A preferred group of test compounds for inclusion in the GAL-R2 expression assay consists of oligonucleotides complementary to various segments of the GAL-R2 nucleic acid sequence. These oligonucleotides should be at least 15 bases in length and should be derived from non-conserved regions of the receptor nucleic acid sequence.

Oligonucleotides which are found to reduce receptor expression may be derivatized or conjugated in order to increase their effectiveness. For example, nucleoside phosphorothioates may be substituted for their natural counterparts (see Cohen, J., Oligodeoxynucleotides, Antisense Inhibitors of Gene Expression, CRC Press (1989)). The oligo-nucleotides may be delivered to a patient in vivo for the purpose of inhibiting GAL-R2 expression. When this is done, it is preferred that the oligonucleotide be administered in a form that enhances its uptake by cells. For example, the oligonucleotide may be delivered by means of a liposome or conjugated to a peptide that is ingested by cells (see e.g., U.S. Pat. Nos. 4,897,355 and 4,394,448; see also non-U.S. patent documents WO 8903849 and EP 0263740). Other methods for enhancing the efficiency of oligonucleotide delivery are well known in the art and are also compatible with the present invention.

Having now described the invention, the same will be more readily understood through reference to the following Examples which are provided by way of illustration and which are not intended to limit the scope of the invention.

EXAMPLES

Example 1

Cloning of Rat Galanin Receptor-2 (GAL-R2)

A PCR-based homology screening strategy was used to isolate novel cDNA sequences encoding G protein-coupled receptors. Sequences likely to encode G protein-coupled receptors were amplified from rat dorsal root ganglia mRNA by reverse transcription PCR using the following primers:

```
                                                  (SEQ ID NO:5)
TM2: 5'-GGCCGTCGACTTCATCGTC(A or T)(A or C)
(T or C)CTI(G or T)CI(T or C)TIGC(A,C,G or T)GAC-3'

(SEQ ID NO:6)
TM7: 5'-(A or G)(C,A or T)(A or T)(A or G)CA(A
or G)TAIATIATIGG(A or G)TT-3'
```

The templates for PCR amplification were synthesized using a "First Strand cDNA Synthesis Kit" (Pharmacia Biotech) and 400 ng of dorsal root ganglia poly A+ RNA. The first strand cDNA thus prepared was diluted two fold with distilled water, heated at 95 C for 3 minutes and quickly chilled on ice. 5 μL of the cDNA thus produced was then amplified with 50 pmoles of each of the TM2 and TM7 primers and 2.5 units of Taq DNA polymerase in 50 mM KCl, 1.5 mM $MgCl_2$, 10 mM Tris (HCl), and 200 μM dNTPs, pH 9.0. The reaction tubes were heated at 95° C. for one min. and then subjected to 40 cycles of denaturation (95° C./1 min), annealing (45° C./1 min) and extension (72° C./1 min). The final extension was performed for 10 min. The amplified fragments were analyzed and size fractionated on a 1.5% agarose gel. Fragments between 400 bp and 1000 bp in length were excised from the gel, purified using a Sephaglas BandPrep kit from Pharmacia, and inserted into a pGEM-T vector from Promega. The recombinant plasmids thus produced were used to transform competent DH5 cells.

Transformed cells were plated on ampicilline-containing 2YT agar plates and recombinant pGEM-T clones were selected by direct colony PCR using primers designed for T7 and SP6 promoters. The PCR conditions were exactly the same as above except 50 pmole each of T7 and SP6 primers were used instead of TM2 and TM7 primers. The annealing temperature was 50 C and 30 cycles were performed. Plasmid DNA was prepared from the clones containing recombinant plasmids using a "Wizard Miniprep DNA Purification System" (Promega Corporation) starting with 4 ml of bacterial culture. The DNA sequence from these clones was determined using the Sanger dideoxynucleotide chain termination method on denatured double-stranded plasmid templates using a T7 sequencing kit from Pharmacia.

The insert DNA fragment of clone 3B-21 was excised from the vector using Sac II and Nde I, isolated on an agarose gel and labeled with $^{32}P$ by random primed synthesis using a Ready-To-Go DNA labeling kit from Pharmacia. This labeled fragment was used to screen a rat brain stem spinal cord cDNA library in ZAP II (Stratagene). Filters were prehybridized for 2 hours at 42° C. in 50% formamide, 5×SSC, 5× Denhardt's solution, 1% glycine and 100 µg/ml denatured and sheared salmon sperm DNA. Hybridization with labeled probe was performed at 42 C for 18 hours in a solution containing 50% formamide, 5×SSC, 1× Denhardt's solution, 0.3% SDS and 100 µg/ml denatured and sheared salmon sperm DNA. Filters were rinsed twice in 2×SSC, 0.1% SDS at room temperature. They were then washed twice for 15 min in 2×SSC, 0.1% SDS at 42 C, twice for 15 min at 42 C in 0.2×SSC, 0.1% SDS, twice with 0.05×SSC, 0.1% SDS at 55 C and finally in the same wash solution at 65 C.

Hybridization-positive phages were purified and their inserts rescued by helper phage mediated excision to yield plasmid DNAs. One clone, 21RSC4, contained the complete coding sequence for the receptor except for 51 bp of the 5' region. This region was obtained by PCR and was then joined at the Bsu36I site at nucleotide number 16 of 21RSC4. Thus, 67 bp at the 5'-end of the coding region of the clone pBS/GALR-2 arose from a PCR-generated fragment.

Example 2

Structural Characteristics of Rat Galanin Receptor-2

The recombinant plasmid pBS/GALR-2 was found to contain an open reading frame of 372 amino acids, flanked by 3' and 5' untranslated regions of, respectively, 289 and 308 bp. The sequence of the open reading frame is shown in FIG. 1 along with the amino acid sequence of the encoded protein. The protein has a molecular mass of 40,700 daltons. Hydropathy analysis of the protein is consistent with a topography of seven transmembrane domains, indicative of the G-protein-coupled receptor family (Sprengel et al., "Hormone Receptors," in Handbook of Receptors and Channels: G Protein-Coupled Receptors, Peroutka, S. J., ed., pp. 153-207, CRC Press (1994)). In addition, sequence analysis revealed that the open reading frame of pBS/GALR-2 contains several conserved structural features/residues found among the members of the neuropeptide receptor family, including: an asparagine in TM1 (Asn43); a leucine (Leu67) and an aspartic acid (Asp 71) in TM2; and an arginine (Arg123) and Tyrosine residue (Tyr124) in TM3. Other features of this GAL-R2 receptor gene are: potential sites for N-glycosylation in the amino terminus (Asn2, Asn11); the presence of several serines and threonines in the carboxyl terminus; and the presence of a second and third intracellular loop, which may serve as potential sites for phosphorylation by protein kinases.

A comparison of the rat GAL-R2 open reading frame with the sequences of human GAL-R2 and GAL-R1 receptors is shown in FIG. 3. Overall, rat GAL-R2 has an identity of about 53% at the nucleotide level and 35.5% at the amino acid level with rat GAL-R1 (Burgevin et al., *J. Mol. Neurosci.* 6:33-41 (1995)) and 34.8% with human GAL-R1 (Habert-Ortoli et al., *Proc. Natl. Acad. Sci. USA* 919780-9783 (1994)). However the sequence homology is higher in the putative transmembrane domains. Respectively, the homologies between the known rat GAL-R1 and GAL-R2 in TM1 to TM7 are 37.5%, 67%, 41.6%, 25%, 50%, 33% and 50%.

Overall, it is apparent that GAL-R2 has a unique sequence that sets it apart from the other G-protein-coupled receptors or other members of the neuropeptide receptor subfamily. The amino acid residues essential for the binding of galanin to the GAL-R1 receptor have been identified as His264, His267, Phe282 and, to a lesser extent, Glu271. Only one of these residues, corresponding to His264, is conserved in GAL-R2.

Example 3

Recombinant Expression of Rat Galanin Receptor-2

To generate a mammalian expression vector, a 1.4 Kb Hind III-Bst-XI restriction fragment from pBS/GALR-2 was isolated and subcloned between the Hind III and BstX-I sites of pcDNA3 from InVitrogen, San Diego, Calif. This expression vector, designated pCDNA3/GALR-2, contains, in addition to the entire receptor coding sequence, 50 bp of 5' untranslated sequence and 288 bp of 3' untranslated sequence. Plasmid DNA for further analysis was prepared using the Qiaprep system from Qiagen.

A. Transient Transfection

HEK293s cells were obtained from Cold Spring Harbor laboratory. They were maintained in culture medium at 37° C., 5% $CO_2$ and diluted 10 fold every 3 days. The cells were inoculated in 80 cm² flasks ($2 \times 10^6$ cells per flask) in Dulbecco's Modified Essential Medium (DMEM, Gibco BRL), supplemented with 10% fetal bovine serum (FBS), 100 U/ml penicillin, 100 µg/ml streptomycin and 0.25 µg/ml fungizone. One day after inoculation, cells were transiently transfected using a modified $CaCl_2$ method (Maniatis, Molecular Cloning: A Laboratory Manual, Cold Spring Harbor Laboratory Press (1989)) and 30 µg of plasmid DNA per flask. The cells were harvested 48 hours post transfection for ligand binding or signal transduction experiments.

B. Stable Transfection

HEK293s cells in 80 cm² flasks were transfected with 30 µg pCDNA3/GALR-2. After 21 days of selection in culture medium containing 600 µg/ml G418 resistant colonies were pooled and expanded for the radioligand binding and signal transduction studies.

Example 4

Binding Characteristics of Recombinantly Expressed Rat GAL-R2

A. Methods

A galanin binding assay was performed on the crude membranes prepared from pcDNA3/GALR-2 transfected cells.

The cells were grown in 150 mm petri dishes to about 80% confluency. Before harvesting, the cells on the petri dishes were washed once with cold PBS (Gibco BRL). Cells were then scraped in ice cold PBS using a Teflon cell scraper. The cells thus harvested were gently centrifuged at 1500×g at 4 C, resuspended in membrane buffer, "MB" (20 mM HEPES pH 7.5 containing 10 µg/ml benzamidine, 5 µg/ml leupeptin, 5 µg/ml soybean trypsin inhibitor and 0.1 mM phenyl methyl sulfonyl fluoride) and were disrupted with a Polytron at a setting of ~20,000 rpm for 30 sec. The disrupted cell suspension was centrifuged at ~100,000×g for 60 minutes at 4 C using a fixed angle rotor in a Beckman L8-70M Ultracentrifuge. The pellet thus obtained was resuspended in the membrane buffer at a concentration of 1.0-1.5 mg/ml, aliquoted and frozen at −80 C until used.

The binding reaction was performed in a total volume of 100 µl of binding buffer (MB+0.4% bovine serum albumin) containing 5-10 µg membrane protein and 0.1 nM $^{125}$I-galanin (2200 Ci/mmol, DupontNEN) with or without unlabeled competitors. Non-specific binding was estimated in the presence of 1 µM of unlabeled galanin. Binding reactions proceeded for 20 min at room temperature and were stopped by filtration through Unifilters-96, GF/B filters (Canberra Packard), using the 96-well Filtermate 196 filtration system from Canberra Packard. Filters were washed 5 times with 0.5 ml of ice cold 20 mM HEPES pH 7.5. The filters were dried at 55° C. for one hour and then 100 µl of µScint-20 (Canberra Packard) was added per well. Filters were counted with the Topcount microplate counter from Canberra Packard.

B. Results

When transfected into HEK293 cells, pCDNA3/GALR-2 resulted in the expression of specific $^{125}$I-galanin binding sites. No specific $^{125}$I-galanin binding sites were generated by the transfection of the vector itself or a control pCDNA3 expression construct encoding a delta-opioid receptor. A pool of stable HEK293 cells expressing the GAL-R2 receptor was generated by selecting pCDNA3/GALR-2 transfected cells using G418 and binding experiments were performed on the membranes of these cells. An example of the results from a binding experiment is shown in FIG. 4.

A single class of saturable $^{125}$I-galanin binding site was detected with an estimated Kd for $^{125}$I-galanin of 1.68±0.43 nM and a Bmax of 1-2 pmol/mg of crude protein. Various galanin related peptides were used in competition experiments performed using $^{125}$I-galanin as a tracer. The competition curves for these peptides are displayed in FIG. 5 and the Ki values of the peptides tested are summarized in Table 1.

TABLE 1

The inhibitory constants of galanin-related peptides for $^{125}$I-galanin binding at GAL-R2

| PEPTIDE | Ki [M] |
| --- | --- |
| Galanin | $2.65 \pm 0.07 \cdot 10^{-9}$ |
| Galanin(1-16) | $1.23 \pm 0.70 \cdot 10^{-8}$ |
| M15 | $3.68 \pm 1.20 \cdot 10^{-8}$ |
| M40 | $8.30 \pm 0.49 \cdot 10^{-9}$ |
| C7 | $1.89 \pm 1.34 \cdot 10^{-7}$ |

The binding of labeled galanin was displaced by galanin and galanin related peptides but not by galanin unrelated ligands (e.g. substance P, vasoactive intestinal polypeptide, angiotensin II and dynorphin). The main difference between rat GAL-R1 and GAL-R2, however, lies in the recognition of the chimeric peptide C7, which is equipotent to galanin at the GAL-R1 receptor but is much less active at GAL-R2.

Example 5

Activation of cAMP

Stable pools of transfected cells were inoculated in 24 well plates and allowed to grow overnight. Before experiments, the cells were washed with PBS at 37 C and then covered with PBS containing 1 mM 3-isobutyl-1-methylxanthine (IBMX). Cells in duplicate wells were stimulated for 10 minutes at 37 C either with forskolin (0.1 mM) alone, or in the presence of various concentrations of galanin or galanin-related peptides. cAMP was extracted in ethanol, lyophilized and resuspended in 0.5 mM assay buffer. Assay of cAMP was performed using either the Biotrack cAMP Enzyme-immunoassay System (Amersham) or the Cyclic AMP [$^3$H] Assay System (Amersham).

Figure 6A:
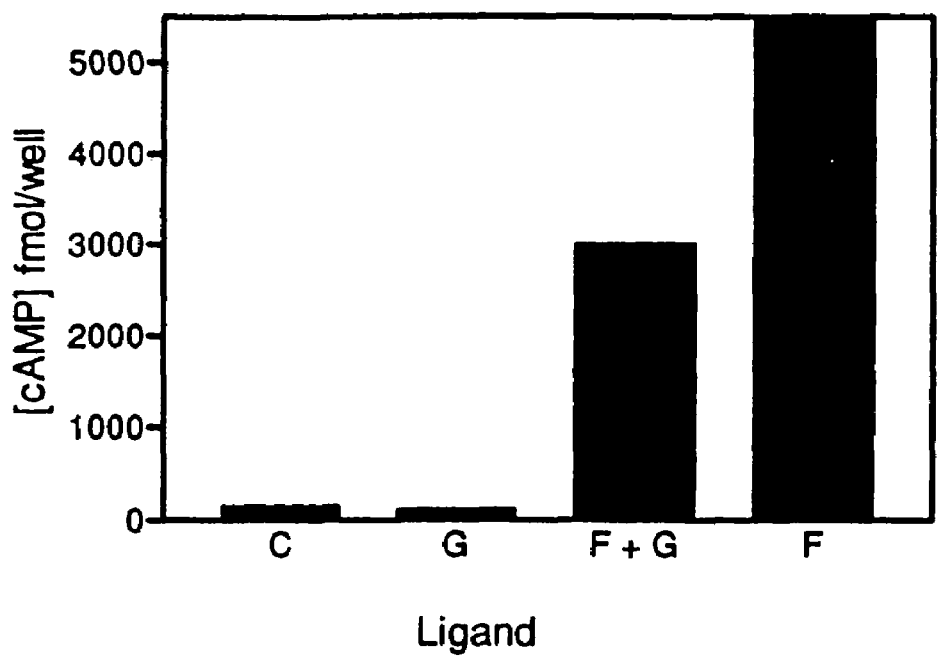
FIG. 6: Galanin attenuated the stimulation of adenyl cyclase by forskolin in a dose-dependent manner in HEK-293 cells expressing GAL-R2. Panel A shows the basal level of cAMP in cells not treated with either forskolin or galanin (C); the effect of 1 µM galanin (G); the effect of 0.1 mM forskolin (F); and the effect of 1 µM galanin+0.1 mM forskolin (F+G). In panel B, cells were incubated in the presence of 0.1 mM forskolin alone or in the presence of forskolin with various concentrations of galanin. Intracellular cAMP was then extracted and measured by enzyme immunoassay as described in Example 4. Results are expressed as percentages, where 100% is the value obtained in the presence of forskolin alone.
Figure 6B:
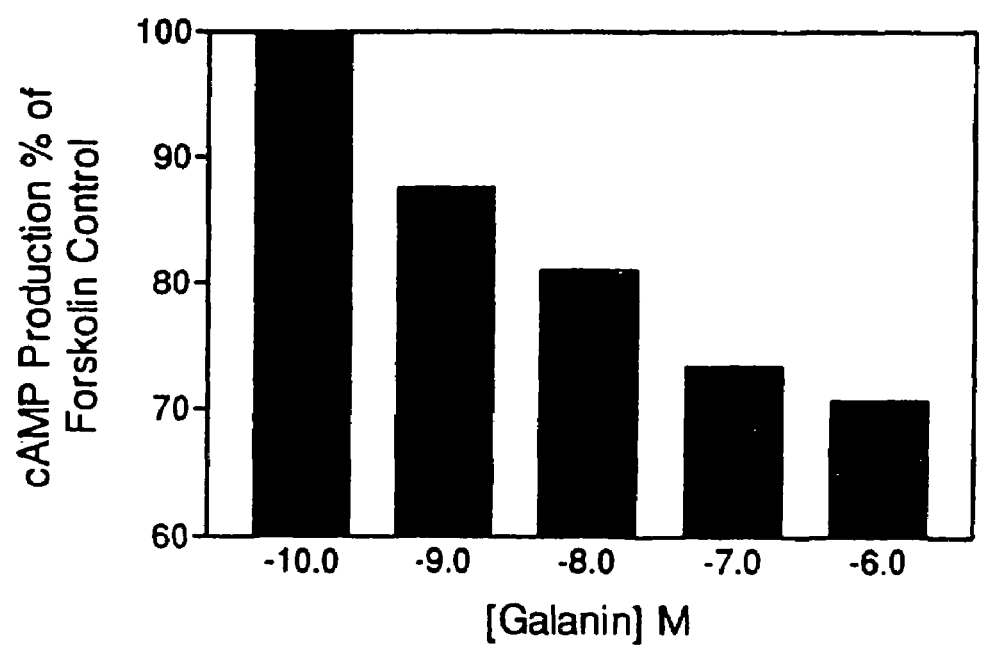

It was found that the activation of rat GAL-R2 in stably transfected HEK293 cells leads to a significant inhibition of forskolin-stimulated accumulation of cAMP and that this inhibition occurs in a concentration-dependent manner (FIG. 6). Untransfected cells failed to exhibit this effect.

Example 6

In Situ Hybridization

A. Methods

Adult male Sprague-Dawley rats (~300 gm; Charles River, St-Constant, Quebec) were sacrificed by decapitation. Brain, pituitary and spinal cord were promptly removed, snap-frozen in isopentane at −40 C for 20 s and stored at −80 C. Frozen tissue was sectioned at 14 µm in a Microm HM 500 M cryostat (Germany) and thaw-mounted onto ProbeOn Plus slides (Fisher Scientific, Montreal, Quebec). Sections were stored at −80 C prior to in situ hybridization.

The plasmid pCDNA3-GALR-2 was linearized using either XbaI or HindIII restriction enzymes which cut in the polylinker on either side of the inserted cDNA. Sense and antisense GAL-R2 riboprobes were transcribed in vitro using either T7 or SP6 RNA polymerases (Pharmacia Biotech), in the presence of [$^{35}$S]UTP (~800 Ci/mmol; Amersham, Oakville, Ontario). Following transcription, the DNA template was digested with DNAse I (Pharmacia). Riboprobes were subsequently purified by phenol/chloro-form/isoamyl alcohol extraction and precipitated in 70% ethanol containing ammonium acetate and tRNA. The quality of labeled riboprobes was verified by polyacrylamide-urea gel electrophoresis.

Sections were postfixed in 4% paraformaldehyde (BDH, Poole, England) in 0.1 M phosphate buffer (pH 7.4) for 10 min at room temperature (RT) and rinsed in 3 changes of 2× standard sodium citrate buffer (SSC: 0.15 M NaCl. 0.015 M sodium citrate, pH 7.0). Sections were then equilibrated in 0.1 M triethanolamine, treated with 0.25% acetic anhydride in triethanolamine, rinsed in 2×SSC and dehydrated in an ethanol series (50-100%). Hybridization was performed in a buffer containing 75% formamide, 600 mM NaCl, 10 mM Tris (pH 7.5), 1 mM EDTA, 1× Denhardt's solution, 50 mg/ml denatured salmon sperm DNA, 50 mg/ml yeast tRNA, 10% dextran sulfate, 20 mM dithiothreitol and [$^{35}$S]UTP-labeled cRNA probes (10×10$^6$ cpm/ml) at 55 C for 18 h in humidified chambers. Following hybridization, slides were rinsed in 2×SSC at RT, treated with 20 mg/ml RNase IA in RNase buffer (10 mM Tris, 500 mM NaCl, 1 mM EDTA, pH 7.5) for 45 min at RT and washed to a final stringency of 0.1×SSC at 65 C. Sections were then dehydrated and exposed to Kodak Biomax MR film for 10 days and/or dipped in Kodak NTB2 emulsion diluted 1:1 with distilled water and exposed for 3-4 weeks at 4 C prior to development and counterstaining with cresyl violet acetate. Neuroanatomical structures were identified according to the Paxinos and Watson rat brain atlas (Paxinos et al., The Rat Brain in Stereotaxic Coordinates, Academic Press, N.Y. (1986)).

B. Results

The highest levels of rat GAL-R2 mRNA expression were observed in dorsal root ganglia with large, intermediate and small diameter cells being specifically labeled. Only diffuse labeling was observed throughout the dorsal and ventral horns of the spinal cord. In the rat brain, the highest densities of GAL-R2 mRNA labeling were detected in the dorsal hippocampus, mammillary bodies and cerebellum (in particular, Purkinje cell layer). More moderate labeling was detected in the pontine nucleus as well as in a specific cranial motor nucleus. Moderate to weak hybridization was detected throughout the cerebral cortices. Other cephalic areas such as the thalamus, the remaining hypothalamus, and basal ganglia were generally devoid of labeling. This distribution differs considerably from that reported for GALR-1 mRNA which is particularly well expressed in the ventral hippocampus, amygdala, supraoptic nucleus, several hypothalamic and thalamic nuclei, lateral parabrachial nucleus and locus coeruleus of rat brain.

The high level of GAL-R2 expression observed in dorsal root ganglia sensory neurons and more moderate levels observed in dorsal horn of the spinal cord is consistent with galanin's role in pain transmission. The presence of high levels of GAL-R2 in dorsal hippocampus and mammillary bodies is consistent with a role in cognitive function.

Example 7

Cloning and Structural Features of Human Galanin Receptor-2

A human genomic DNA library prepared from human placenta (Clonetech) in EMBL-3 vector was screened with a random labeled fragment (labeled with T7-Quick-Prime labeling kit cat. #27-9252-01, Pharmacia Biotech.) containing the complete coding region of rat GALR-2 cDNA. The prehybridization and hybridization conditions were as follows:

Prehybridization: 50% formamide, 5× Denhardt's solution, 5×SSC, 1% glycine, 100 g/ml sheared and denatured salmon sperm DNA at 42° C. for 5 hours.

Hybridization: 50% formamide, 1× Denhardt's solution, 5×SSC, 0.3% SDS, 100 g/ml sheared and denatured salmon sperm DNA overnight at 42° C.

Wash: A wash step was performed from the low stringency of 2×SSC, 0.1% SDS at 42° C. to the highest stringency of 0.2×SSC, 0.1% SDS at 60° C. (65° C. for Southern blots).

Eight positive clones were identified which were processed for secondary screening under hybridization and washing conditions identical to the first. The secondary screening resulted in identification of four clones; the other four clones were considered false-positive. The four positive clones were processed for tertiary and quarternary screening in order to obtain pure clones.

DNA was purified from the four pure clones discussed above and was processed for restriction analysis and Southern blot hybridization in order to identify smaller fragments which yield a positive signal. Three positively hybridizing bands (of estimated sizes ~5 kb, ~3.2 kb and ~0.7 kb) generated by the cleavage with Sac I and Rsa I restriction endonucleases (Pharmacia Biotech.) were identified by Southern blot hybridization. These bands were excised from the gel and subcloned into either Sac I or Eco RV digested pBlueScript KS(−) plasmid. The plasmid constructs were subjected to sequencing by Sanger dideoxy sequencing method (T7 Sequencing kit, Pharmacia Biotech. Cat. #27-1682-01) and the ABI Prizm Cycle Sequencing Kit (Cat. #402079, Perkin-Elmer) and the composite sequence was constructed.

The nucleotide sequence for human GALR-2 gene is depicted in FIG. 2. An open reading frame of 1155 nucleotides is present putatively encoding a protein of 385 amino acids with a calculated molecular mass of 41478 kD. There is a putative intron of more than 1000 nucleotide in length after base number 420. The intronic sequence has been removed from the finalized sequence reproduced in FIG. 2. The exon-intron boundaries were determined based upon the consensus sequences around 5' and 3' splice sites in vertebrate pre-mRNAs (Lodish et al. Molecular Cell Biology $3^{rd}$ Ed. Scientific American Books, pp 500; FIG. 4). At the protein level, 84.4% amino acids are identical between rat and human GALR-2; the identity between the human GALR-2 and the rat or human GALR-1 is about 34%.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

Deposit of Biological Material

The plasmid HUMAN GALR-2 has been deposited under the Budapest Treaty at "Deutsche Sammlung von Mikroorganismen und Zellkulturen" (DSMZ), Braunschweig, Germany. The deposit number is DSM 11632, and the date of deposit is 26 Jun. 1997.

SEQUENCE LISTING

<160> NUMBER OF SEQ ID NOS: 8

<210> SEQ ID NO 1
<211> LENGTH: 1714
<212> TYPE: DNA
<213> ORGANISM: rat GAL-2R sequence

<400> SEQUENCE: 1
ccgcgcgcac accgctccct ccacacctcc aggggagtg agccactcaa gtctaaagca    60

```
gagcgagtcc caggacttga gcgcgggaag cgaatggagt cagggtcatt cgattgcacc      120
tctctcgact gcgggccgga gcggggtacc atcctacact ctgggtgctc cctcctcctc      180
ccgtcccccg cgcacccctc ccctgtctcc tggagctcgg cagtctcgct ggggcgctgc      240
agcgagggag cagcgtgctc accaaggacc cggacagctg cgggagcggc gtccactttg      300
gtgataccat gaatggctcc ggcagccagg gcgcggagaa cacgagccag gaaggcagta      360
gcggcggctg cagcctgag gcggtccttg taccccctatt tttcgcgctc atcttcctcg      420
tgggcaccgt gggcaacgcg ctggtgctgg cggtgctgct gcgcggcggc caggcggtca      480
gcaccaccaa cctgttcatc ctcaacctgg gcgtggccga cctgtgtttc atcctgtgct      540
gcgtgccttt ccaggccacc atctacaccc tggacgactg ggtgttcggc tcgctgctct      600
gcaaggctgt tcatttcctc atctttctca ctatgcacgc cagcagcttc acgctggccg      660
ccgtctccct ggacaggtat ctggccatcg ctacccgct gcactcccga gagttgcgca      720
cacctcgaaa cgcgctggcc gccatcgggc tcatctgggg gctagcactg ctcttctccg      780
ggccctacct gagctactac cgtcagtcgc agctggccaa cctgacagta tgccacccag      840
catggagcgc acctcgacgt cgagccatgg acctctgcac cttcgtcttt agctacctgc      900
tgccagtgct agtcctcagt ctgacctatg cgcgtaccct gcgctacctc tggcgcacag      960
tcgacccggt gactgcaggc tcaggttccc agcgcgccaa acgcaaggtg acacggatga     1020
tcatcatcgt ggcggtgctt ttctgcctct gttggatgcc ccaccacgcg cttatcctct     1080
gcgtgtggtt tggtcgcttc ccgctcacgc gtgccactta cgcgttgcgc atcctttcac     1140
acctagtttc ctatgccaac tcctgtgtca accccatcgt ttacgctctg gtctccaagc     1200
atttccgtaa aggtttccgc aaaatctgcg cgggcctgct cgccctgcc ccgaggcgag     1260 cttcgggccg agtgagcatc ctggcgcctg ggaaccatag tggcagcatg ctggaacagg     1320
aatccacaga cctgacacag gtgagcgagg cagccgggcc ccttgtccca ccaccccgcac     1380 ttcccaactg cacagcctcg agtagaaccc tggatccggc ttgttaaagg accaaagggc     1440
atctaacagc ttctagacag tgtggcccga ggatccctgg gggttatgct tgaacgttac     1500
agggttgagg ctaaagactg aggattgatt gtagggaacc tccagttatt aaacggtgcg     1560
gattgctaga gggtggcata gtccttcaat cctggcaccc gaaaagcaga tgcaggagca     1620
ggagcaggag caaagccagc catggagttt gaggcctgct tgaactacct gagatccaat     1680
aataaaacat ttcatatgct ctcgtgccga attc                                 1714

<210> SEQ ID NO 2
<211> LENGTH: 372
<212> TYPE: PRT
<213> ORGANISM: rat GAL-2R sequence

<400> SEQUENCE: 2

Met Asn Gly Ser Gly Ser Gln Gly Ala Glu Asn Thr Ser Gln Glu Gly
1               5                   10                  15

Ser Ser Gly Gly Trp Gln Pro Glu Ala Val Leu Val Pro Leu Phe Phe
            20                  25                  30

Ala Leu Ile Phe Leu Val Gly Thr Val Gly Asn Ala Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80
```

```
Phe Gln Ala Thr Ile Tyr Thr Leu Asp Asp Trp Val Phe Gly Ser Leu
                85                  90                  95
Leu Cys Lys Ala Val His Phe Leu Ile Phe Leu Thr Met His Ala Ser
            100                 105                 110
Ser Phe Thr Leu Ala Ala Val Ser Leu Asp Arg Tyr Leu Ala Ile Arg
        115                 120                 125
Tyr Pro Leu His Ser Arg Glu Leu Arg Thr Pro Arg Asn Ala Leu Ala
    130                 135                 140
Ala Ile Gly Leu Ile Trp Gly Leu Ala Leu Leu Phe Ser Gly Pro Tyr
145                 150                 155                 160
Leu Ser Tyr Tyr Arg Gln Ser Gln Leu Ala Asn Leu Thr Val Cys His
                165                 170                 175
Pro Ala Trp Ser Ala Pro Arg Arg Ala Met Asp Leu Cys Thr Phe
            180                 185                 190
Val Phe Ser Tyr Leu Leu Pro Val Leu Val Leu Ser Leu Thr Tyr Ala
        195                 200                 205
Arg Thr Leu Arg Tyr Leu Trp Arg Thr Val Asp Pro Val Thr Ala Gly
    210                 215                 220
Ser Gly Ser Gln Arg Ala Lys Arg Lys Val Thr Arg Met Ile Ile Ile
225                 230                 235                 240
Val Ala Val Leu Phe Cys Leu Cys Trp Met Pro His His Ala Leu Ile
                245                 250                 255
Leu Cys Val Trp Phe Gly Arg Phe Pro Leu Thr Arg Ala Thr Tyr Ala
            260                 265                 270
Leu Arg Ile Leu Ser His Leu Val Ser Tyr Ala Asn Ser Cys Val Asn
        275                 280                 285
Pro Ile Val Tyr Ala Leu Val Ser Lys His Phe Arg Lys Gly Phe Arg
    290                 295                 300
Lys Ile Cys Ala Gly Leu Leu Arg Pro Ala Pro Arg Arg Ala Ser Gly
305                 310                 315                 320
Arg Val Ser Ile Leu Ala Pro Gly Asn His Ser Gly Ser Met Leu Glu
                325                 330                 335
Gln Glu Ser Thr Asp Leu Thr Gln Val Ser Glu Ala Ala Gly Pro Leu
            340                 345                 350
Val Pro Pro Pro Ala Leu Pro Asn Cys Thr Ala Ser Ser Arg Thr Leu
        355                 360                 365
Asp Pro Ala Cys
    370

<210> SEQ ID NO 3
<211> LENGTH: 1219
<212> TYPE: DNA
<213> ORGANISM: human GAL-2R sequence

<400> SEQUENCE: 3
gggtcagcgg caccatgaac gtctcgggct gcccagggge cgggaacgcg agccaggcgg      60
gcggcggggg aggctggcac cccgaggcgg tcatcgtgcc cctgctcttc gcgctcatct     120
tcctcgtggg caccgtgggc aacacgctgg tgctggcggt gctgctgcgc ggcggccagg     180
cggtcagcac taccaacctg ttcatcctta acctgggcgt ggccgacctg tgtttcatcc     240
tgtgctgcgt gcccttccag gccaccatct acaccctgga cgactgggtg ttcggctcgc     300
tgctgtgcaa ggcggtgcac ttcctcatct tcctcaccat gcacgccagc agcttcacgc     360
tggccgccgt ctccctggac aggtatttgg ccatccgcta cccgctgcac tcccgcgagc     420
```

```
tgcgcacgcc tcgaaacgcg ctggcagcca tcgggctcat ctgggggctg tcgctgctct      480
tctccgggcc ctacctgagc tactaccgcc agtcgcagct ggccaacctg accgtgtgcc      540
atcccgcgtg gagcgcccct cgccgccgcg ccatggacat ctgcaccttc gtcttcagct      600
acctgcttcc tgtgctggtt ctcggcctga cctacgcgcg caccttgcgc tacctctggc      660
gcgccgtcga cccggtggcc gcgggctcgg gtgcccggcg cgccaagcgc aaggtgacac      720
gcatgatcct catcgtggcc gcgctcttct gcctctgctg gatgccccac cacgcgctca      780
tcctctgcgt gtggttcggc cagttccgc tcacgcgcgc cacttatgcg cttcgcatcc       840
tctcgcacct ggtctcctac gccaactcct gcgtcaaccc catcgtttac gcgctggtct      900
ccaagcactt ccgcaaaggc ttccgcacga tctgcgcggg cctgctgggc cgtgccccag      960
gccgagcctc gggccgtgtg tgcgctgccg cgcggggcac ccacagtggc agcgtgttgg     1020
agcgcgagtc cagcgacctg ttgcacatga gcgaggcggg gggggccctt cgtccctgcc     1080
ccggcgcttc ccagccatgc atcctcgagc cctgtcctgg cccgtcctgg cagggcccaa     1140
aggcagggca gacaggcatt cctgacggtt gatgtggcct tgaaaggcac ttagcgggcg     1200
cctgggatgt acagagttg                                                 1219
```

<210> SEQ ID NO 4
<211> LENGTH: 385
<212> TYPE: PRT
<213> ORGANISM: human GAL-2R sequence

<400> SEQUENCE: 4

```
Met Asn Val Ser Gly Cys Pro Gly Ala Gly Asn Ala Ser Gln Ala Gly
 1               5                  10                  15

Gly Gly Gly Gly Trp His Pro Glu Ala Val Ile Val Pro Leu Leu Phe
            20                  25                  30

Ala Leu Ile Phe Leu Val Gly Thr Val Gly Asn Thr Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Gly Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Gly Leu Ile Trp Gly Leu Ser Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Ala Met Asp Ile Cys Thr Phe
            180                 185                 190

Val Phe Ser Tyr Leu Leu Pro Val Leu Val Leu Gly Leu Thr Tyr Ala
        195                 200                 205

Arg Thr Leu Arg Tyr Leu Trp Arg Ala Val Asp Pro Val Ala Ala Gly
    210                 215                 220
```

```
Ser Gly Ala Arg Arg Ala Lys Arg Lys Val Thr Arg Met Ile Leu Ile
225                 230                 235                 240

Val Ala Ala Leu Phe Cys Leu Cys Trp Met Pro His His Ala Leu Ile
                245                 250                 255

Leu Cys Val Trp Phe Gly Gln Phe Pro Leu Thr Arg Ala Thr Tyr Ala
            260                 265                 270

Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
    290                 295                 300

Thr Ile Cys Ala Gly Leu Leu Gly Arg Ala Pro Gly Arg Ala Ser Gly
305                 310                 315                 320

Arg Val Cys Ala Ala Ala Arg Gly Thr His Ser Gly Ser Val Leu Glu
                325                 330                 335

Arg Glu Ser Ser Asp Leu Leu His Met Ser Glu Ala Ala Gly Ala Leu
            340                 345                 350

Arg Pro Cys Pro Gly Ala Ser Gln Pro Cys Ile Leu Glu Pro Cys Pro
        355                 360                 365

Gly Pro Ser Trp Gln Gly Pro Lys Ala Gly Gln Thr Gly Ile Pro Asp
    370                 375                 380

Gly
385

<210> SEQ ID NO 5
<211> LENGTH: 345
<212> TYPE: PRT
<213> ORGANISM: rat GAL-1R sequence

<400> SEQUENCE: 5

Met Glu Leu Ala Pro Val Asn Leu Ser Glu Gly Asn Gly Ser Asp Pro
1               5                   10                  15

Glu Pro Pro Ala Glu Pro Arg Pro Leu Phe Gly Ile Gly Val Glu Asn
                20                  25                  30

Phe Ile Thr Leu Val Val Phe Gly Leu Ile Phe Ala Met Gly Val Leu
            35                  40                  45

Gly Asn Ser Leu Val Ile Thr Val Leu Ala Arg Ser Lys Pro Gly Lys
        50                  55                  60

Pro Arg Ser Thr Thr Asn Leu Phe Ile Leu Asn Leu Ser Ile Ala Asp
65                  70                  75                  80

Leu Ala Tyr Leu Leu Phe Cys Ile Pro Phe Gln Ala Thr Val Tyr Ala
                85                  90                  95

Leu Pro Thr Trp Val Leu Gly Ala Phe Ile Cys Lys Phe Ile His Tyr
            100                 105                 110

Phe Phe Thr Val Ser Met Leu Val Ser Ile Phe Thr Leu Ala Ala Met
        115                 120                 125

Ser Val Asp Arg Tyr Val Ala Ile Val His Ser Arg Arg Ser Ser Ser
    130                 135                 140

Leu Arg Val Ser Arg Asn Ala Leu Leu Gly Val Gly Phe Ile Trp Ala
145                 150                 155                 160

Leu Ser Ile Ala Met Ala Ser Pro Val Ala Tyr Tyr Gln Arg Leu Phe
                165                 170                 175

His Arg Asp Ser Asn Gln Thr Phe Cys Trp Glu His Trp Pro Asn Gln
            180                 185                 190

Leu His Lys Lys Ala Tyr Val Val Cys Thr Phe Val Phe Gly Tyr Leu
        195                 200                 205
```

```
Leu Pro Leu Leu Leu Ile Cys Phe Cys Tyr Ala Lys Val Leu Asn His
    210                 215                 220

Leu His Lys Lys Leu Lys Asn Met Ser Lys Lys Ser Glu Ala Ser Lys
225                 230                 235                 240

Lys Lys Thr Ala Gln Thr Val Leu Val Val Val Val Phe Gly Ile
                245                 250                 255

Ser Trp Leu Pro His His Val Ile His Leu Trp Ala Glu Phe Gly Ala
            260                 265                 270

Phe Pro Leu Thr Pro Ala Ser Phe Phe Arg Ile Thr Ala His Cys
        275                 280                 285

Leu Ala Tyr Ser Asn Ser Ser Val Asn Pro Ile Ile Tyr Ala Phe Leu
    290                 295                 300

Ser Glu Asn Phe Arg Lys Ala Tyr Lys Gln Val Phe Lys Cys Arg Val
305                 310                 315                 320

Asn Glu Ser Pro His Gly Asp Ala Lys Glu Lys Asn Arg Ile Asp Thr
                325                 330                 335

Pro Pro Ser Thr Asn Cys Thr His Val
                340                 345

<210> SEQ ID NO 6
<211> LENGTH: 349
<212> TYPE: PRT
<213> ORGANISM: human GAL-1R sequence

<400> SEQUENCE: 6

Met Glu Leu Ala Val Gly Asn Leu Ser Glu Gly Asn Ala Ser Cys Pro
1               5                   10                  15

Glu Pro Pro Ala Pro Glu Pro Gly Pro Leu Phe Gly Ile Gly Val Glu
            20                  25                  30

Asn Phe Val Thr Leu Val Val Phe Gly Leu Ile Phe Ala Leu Gly Val
        35                  40                  45

Leu Gly Asn Ser Leu Val Ile Thr Val Leu Ala Arg Ser Lys Pro Gly
50                  55                  60

Lys Pro Arg Ser Thr Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
            85                  90                  95

Ala Leu Pro Thr Trp Val Leu Gly Ala Phe Ile Cys Lys Phe Ile His
        100                 105                 110

Tyr Phe Phe Thr Val Ser Met Leu Val Ser Ile Phe Thr Leu Ala Ala
    115                 120                 125

Met Ser Val Asp Arg Tyr Val Ala Ile Val His Ser Arg Arg Ser Ser
    130                 135                 140

Ser Leu Arg Val Ser Arg Asn Ala Leu Leu Gly Val Gly Cys Ile Trp
145                 150                 155                 160

Ala Leu Ser Ile Ala Met Ala Ser Pro Val Ala Tyr His Gln Gly Leu
            165                 170                 175

Phe His Pro Arg Ala Ser Asn Gln Thr Phe Cys Trp Glu Gln Trp Pro
        180                 185                 190

Asp Pro Arg His Lys Lys Ala Tyr Val Val Cys Thr Phe Val Phe Gly
    195                 200                 205

Tyr Leu Leu Pro Leu Leu Leu Ile Cys Phe Cys Tyr Ala Lys Val Leu
    210                 215                 220

Asn His Leu His Lys Lys Leu Lys Asn Met Ser Lys Lys Ser Glu Ala
```

```
                225                 230                 235                 240
Ser Lys Lys Lys Thr Ala Gln Thr Val Leu Val Val Val Val Phe
                    245                 250                 255

Gly Ile Ser Trp Leu Pro His His Ile Ile His Leu Trp Ala Glu Phe
                260                 265                 270

Gly Val Phe Pro Leu Thr Pro Ala Ser Phe Leu Phe Arg Ile Thr Ala
                275                 280                 285

His Cys Leu Ala Tyr Ser Asn Ser Ser Val Asn Pro Ile Ile Tyr Ala
            290                 295                 300

Phe Leu Ser Glu Asn Phe Arg Lys Ala Tyr Lys Gln Val Phe Lys Cys
305                 310                 315                 320

His Ile Arg Lys Asp Ser His Leu Ser Asp Thr Lys Glu Asn Lys Ser
                325                 330                 335

Arg Ile Asp Thr Pro Pro Ser Thr Asn Cys Thr His Val
                340                 345

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: GAL-2R
      primer
<220> FEATURE:
<221> NAME/KEY: misc_feature
<222> LOCATION: (20)
<223> OTHER INFORMATION: w is a or t/u
<220> FEATURE:
<221> NAME/KEY: misc_feature
<222> LOCATION: (21)
<223> OTHER INFORMATION: m is a or c
<220> FEATURE:
<221> NAME/KEY: misc_feature
<222> LOCATION: (22)
<223> OTHER INFORMATION: y is t/u or c
<220> FEATURE:
<221> NAME/KEY: misc_feature
<222> LOCATION: (25)
<223> OTHER INFORMATION: n is inosine
<220> FEATURE:
<221> NAME/KEY: misc_feature
<222> LOCATION: (26)
<223> OTHER INFORMATION: k is g or t/u
<220> FEATURE:
<221> NAME/KEY: misc_feature
<222> LOCATION: (28)
<223> OTHER INFORMATION: n is inosine
<220> FEATURE:
<221> NAME/KEY: misc_feature
<222> LOCATION: (29)
<223> OTHER INFORMATION: y is t/u or c
<220> FEATURE:
<221> NAME/KEY: misc_feature
<222> LOCATION: (31)
<223> OTHER INFORMATION: n is inosine
<220> FEATURE:
<221> NAME/KEY: misc_feature
<222> LOCATION: (34)
<223> OTHER INFORMATION: n is a, g, c, or t/u

<400> SEQUENCE: 7
ggccgtcgac ttcatcgtcw myctnkcnyt ngcngac                              37

<210> SEQ ID NO 8
<211> LENGTH: 21
<212> TYPE: DNA
<213> ORGANISM: artificial sequence
<220> FEATURE:
<223> OTHER INFORMATION: Description of Artificial Sequence: GAL-2R
```

```
      primer
<220> FEATURE:
<221> NAME/KEY: misc_feature
<222> LOCATION: (1)
<223> OTHER INFORMATION: r is g or a
<220> FEATURE:
<221> NAME/KEY: misc_feature
<222> LOCATION: (2)
<223> OTHER INFORMATION: h is c, a, or t/u
<220> FEATURE:
<221> NAME/KEY: misc_feature
<222> LOCATION: (3)
<223> OTHER INFORMATION: w is a or t/u
<220> FEATURE:
<221> NAME/KEY: misc_feature
<222> LOCATION: (4)
<223> OTHER INFORMATION: r is g or a
<220> FEATURE:
<221> NAME/KEY: misc_feature
<222> LOCATION: (7)
<223> OTHER INFORMATION: r is g or a
<220> FEATURE:
<221> NAME/KEY: misc_feature
<222> LOCATION: (10)
<223> OTHER INFORMATION: n is inosine
<220> FEATURE:
<221> NAME/KEY: misc_feature
<222> LOCATION: (13)
<223> OTHER INFORMATION: n is inosine
<220> FEATURE:
<221> NAME/KEY: misc_feature
<222> LOCATION: (16)
<223> OTHER INFORMATION: n is inosine
<220> FEATURE:
<221> NAME/KEY: misc_feature
<222> LOCATION: (19)
<223> OTHER INFORMATION: r is g or a

<400> SEQUENCE: 8
rhwrcartan atnatnggrt t                                        21
```

What is claimed is:

1. A method for assaying a test compound for its ability to bind GAL-R2 comprising: incubating a source containing GAL-R2 but substantially free of other galanin receptors with a ligand known to bind to GAL-R2; and the test compound; and determining whether the ligand binding to GAL-R2 is displaced by the test compound, wherein displacement of ligand binding indicates that the test compound binds to GAL-R2, wherein the source of GAL-R2 is a cell transformed with a vector for expressing rat GAL-R2, wherein the vector comprises a polynucleotide encoding a protein comprising SEQ ID NO:2.

2. A method of claim 1 wherein the polynucleotide comprises SEQ ID NO:1.

3. A method for assaying a test compound for its ability to bind GAL-R2 comprising: incubating a source containing GAL-R2 but substantially free of other galanin receptors with a ligand known to bind GAL-R2 and the test compound; and determining whether the ligand binding to GAL-R2 is displaced by the test compound, wherein displacement of ligand binding indicates that the test compound binds to GAL-R2 wherein the source containing GAL-R2 is a membrane preparation from a cell transformed with a vector for expressing rat GAL-R2, wherein the vector comprises a polynucleotide encoding a protein comprising SEQ ID NO:2.

4. A method of claim 3 wherein the polynucleotide comprises SEQ ID NO:1.

5. A method for assaying a test compound for its ability to bind GAL-R2 comprising: incubating a source containing GAL-R2 but substantially free of other galanin receptors with a ligand known to bind GAL-R2 and the test compound; and determining whether the ligand binding to GAL-R2 is displaced by the test compound, wherein displacement of ligand binding indicates that the test compound binds to GAL-R2 wherein the source containing GAL-R2 is a cell transformed with a vector for expressing human GAL-R2, wherein the vector comprises a polynucleotide encoding a protein comprising SEQ ID NO:4.

6. A method of claim 5 wherein the polynucleotide comprises SEQ ID NO:3.

7. A method for assaying a test compound for its ability to bind GAL-R2 comprising: incubating a source containing GAL-R2 but substantially free of other galanin receptors with a ligand known to bind GAL-R2 and the test compound; and determining whether the ligand binding to GAL-R2 is displaced by the test compound, wherein displacement of ligand binding indicates that the test compound binds to GAL-R2 wherein the source containing GAL-R2 is a membrane preparation from a cell transformed with a vector for expressing human GAL-R2, wherein the vector comprises a polynucleotide encoding a protein comprising SEQ ID NO:4.

8. A method of claim 7 wherein the polynucleotide comprises SEQ ID NO:3.

9. A method for assaying a test compound for its ability to bind GAL-R2 comprising: incubating a source containing GAL-R2 comprising SEQ ID NO:2 but substanially free of the other galanin receptors with: a ligand known to bind GAL-R2; and the test compound; and determining whether the ligand binding to GAL-R2 is displaced by the test compound, wherein displacement of ligand binding indicates that the test compound binds to the GAL-R2.

10. A method for assaying a test compound for its ability to bind GAL-R2 comprising: incubating a source containing GAL-R2 comprising SEQ ID NO:4 but substanially free of the other galanin receptors with: a ligand known to bind GAL-R2; and the test compound; and determining whether the ligand binding to GAL-R2 is displaced by the test compound, wherein displacement of ligand binding indicates that the test compound binds to the GAL-R2.

* * * * *